United States Patent
Shin et al.

(10) Patent No.: US 7,081,546 B2
(45) Date of Patent: Jul. 25, 2006

(54) PROCESS FOR PREPARING A 5-HYDROXY-3-OXO-HEXANOIC ACID DERIVATIVE

(75) Inventors: Hyun-Ik Shin, Daejeon (KR); Bo-Seung Choi, Daejeon (KR)

(73) Assignee: LG Life Sciences Ltd., Seoul (KR)

( * ) Notice: Subject to any disclaimer, the term of this patent is extended or adjusted under 35 U.S.C. 154(b) by 0 days.

(21) Appl. No.: 10/540,524

(22) PCT Filed: Nov. 17, 2003

(86) PCT No.: PCT/KR03/02470

§ 371 (c)(1),
(2), (4) Date: Jun. 24, 2005

(87) PCT Pub. No.: WO2004/063132

PCT Pub. Date: Jul. 29, 2004

(65) Prior Publication Data

US 2006/0079710 A1    Apr. 13, 2006

(30) Foreign Application Priority Data

Nov. 17, 2003 (KR) .................... 10-2003-0002991

(51) Int. Cl.
*C07C 49/173* (2006.01)

(52) U.S. Cl. .................................... 560/174

(58) Field of Classification Search ................ 560/174
See application file for complete search history.

(56) References Cited

U.S. PATENT DOCUMENTS

| 5,594,153 A | 1/1997 | Thottathil et al. |
| 6,340,767 B1 | 1/2002 | Nishiyama et al. |
| 6,399,339 B1 | 6/2002 | Wolberg et al. |

FOREIGN PATENT DOCUMENTS

EP       1024139 A    10/2000

OTHER PUBLICATIONS

Scheffler et al., "Preparation and stereoselective hydrogenation of chiral (4-hydroxytetrafuranylidene)carboxylates: a new formal entry to functional anti- and syn-3, 5-dihydroxy esters"Tetrahedron Letters (2002), 43(15), 2679-2682.

*Primary Examiner*—Kamal A. Saeed
(74) *Attorney, Agent, or Firm*—Birch, Stewart, Kolasch & Birch, LLP

(57) ABSTRACT

The present invention is related to a novel process for preparing an optically active 5-hydroxy-3-oxo-hexanoic acid derivative or its tautomer which is useful intermediate for preparing statins such as atorvastatin and rosuvastatin. Blaise reaction of (S)-4-halo-3-hydroxybutyronitrile with -haloacetate is utilized as a key reaction to provide the product with minimal formation of side products and in good yield.

16 Claims, No Drawings

PROCESS FOR PREPARING A 5-HYDROXY-3-OXO-HEXANOIC ACID DERIVATIVE

TECHNICAL FIELD

The present invention is related to a novel process for preparing an optically active 5-hydroxy-3-oxo-hexanoic acid derivative of the following formula (1):

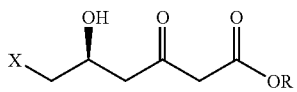

(1)

or its tautomer, in which

R represents hydrogen, saturated-$C_1$–$C_4$-alkyl, or unsaturated-$C_2$–$C_4$-alkyl, and X represents halogen such as Br, Cl, I, etc., which is a useful intermediate for preparing statins such as atorvastatin, rosuvastatin, etc. known as an agent for the treatment of hypercholesterolemia and hyperlipidemia.

BACKGROUND ART

In the existing process for preparing the above compound of formula (1), an optically active 3-hydroxyester compound was reacted with lithium enolate of t-butylacetate generated by the treatment of lithium diisopropylamide (LDA) or lithium hexamethyldisilazide (LHMDS) at low temperature (−78° C.) to provide compound of formula (1) (see: U.S. Pat. No. 5,278,313). Recently, a similar reaction to the above was successfully carried out by the addition of Grignard reagent before Claisen condensation. This condition enabled the reaction performed at 5° C. (see: European Patent Laid-open Publication No. 1104750).

The above processes, however, used excess lithium hexamethyldisilazide or lithium diisopropylamide that has some problems to be used in the industrial production. Moreover, the former route is complicated by the formation of significant amount of undesired side products even at very low temperature (see: *Tetraehdron Lett.*, 2002, 43, 2679–2682). The latter precedent results in pretty low yield comparing to the former process. The only advantage of the latter process is that the reaction can be executed at 5° C.

DISCLOSURE OF THE INVENTION

The present inventors have conducted extensive researches to overcome the above problems of the existing processes. As a result, the inventors have developed a novel process for preparing the compound of formula (1) by Blaise reaction of (S)-4-halo-3-hydroxybutyronitrile and α-haloacetate using zinc metal activated in situ by an organic acid or its derivative. This novel route resulted in the formation of side products to a minimal quantity and all the reactions are executed at around ambient temperature or above.

Therefore, the present invention provides an effective process for preparing the compound of formula (1), as defined above, or its tautomer using Blaise reaction which uses zinc metal activated in situ by an organic acid or its derivative.

BEST MODE FOR CARRYING OUT THE INVENTION

The present invention is related to a process for preparing the compound of formula (1):

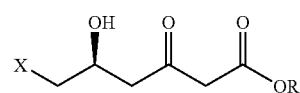

(1)

or its tautomer, in which

R represents hydrogen, saturated-$C_1$–$C_4$-alkyl, or unsaturated-$C_2$–$C_4$-alkyl, and X represents halogen such as Br, Cl, I, etc., which comprises the following steps:

1) (S)-4-halo-3-hydroxybutyronitile derivative of the following formula (2)

(2)

in which

X is as defined as above, and

P represents hydrogen or a hydroxy-protecting group, is reacted with an α-haloacetate compound of the following formula (3)

$$YCH_2CO_2R \qquad (3)$$

in which

R is as defined above, and

Y represents Br or I, in the presence of zinc metal activated by an organic acid or its derivative in an organic solvent and 2) the product of step 1) is hydrolyzed in the presence of aqueous acid solution.

The tautomer of the compound of formula (1) means the enol form compound of the following formula (1a):

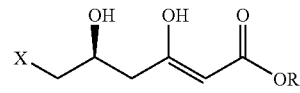

(1a)

However, the compound of formula (1) is obtained as the main product of the process according to the present invention.

The key feature of the present invention is that the nitrile functionality of formula (2) is subjected to Blaise reaction of α-haloacetate of formula (3) using zinc metal activated by an organic acid or its derivative to introduce the β-ketoester group of formula (1). The reaction mechanism can be depicted as the following Reaction Scheme 1:

Reaction Scheme 1

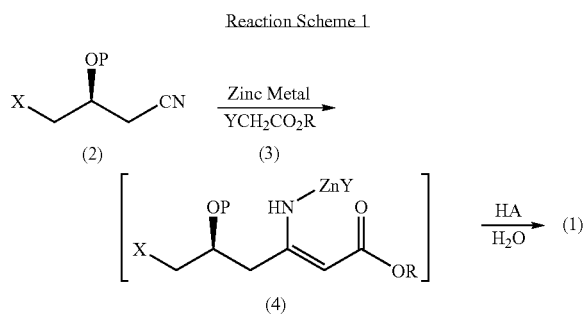

In the process of the present invention, to a stirred suspension of zinc metal in organic solvent is added catalytic amount of an organic acid or its derivative and the mixture is stirred under reflux to activate the zinc metal. To the mixture are added slowly the nitrile compound of formula (2) and the α-haloacetate compound of formula (3) in order to prepare the enamine intermediate of formula (4). After the completion of the reaction, the whole mixture is hydrolyzed by aqueous acid solution to provide the desired compound of formula (1). The respective reaction conditions will be explained in more detail below.

The group P in formula (2) represents hydrogen or a hydroxy-protecting group. The hydroxy-protecting group includes $SiRR^1R^2$ wherein R is as defined above, and $R^1$ and $R^2$ each represent hydrogen, saturated-$C_1$–$C_6$-alkyl, unsaturated-$C_2$–$C_6$-alkyl, or $C_6$–$C_{12}$-aromatic group, and ethoxyethyl, and tetrahydropyranyl. The group $SiRR^1R^2$ preferably includes trimethylsilyl (TMS), triethylsilyl (TES), t-butyldimethylsilyl (TBDMS), and t-butyldiphenylsilyl (TBDPS). Trimethylsilyl is the most preferable as the hydroxy-protecting group in the aspect of purity and yield.

As reaction solvent, tetrahydrofuran, benzene, toluene and ether may be used. Among them, tetrahydrofuran is the most preferable in terms of purity and yield.

The α-haloacetate compound of formula (3) is added dropwise over 0.5 to 2.0 hours, and the purity and yield are the most satisfactory when the addition time is between 1.0 and 1.5 hour. It is preferable to use the compound of formula (3) in an amount of 1.0 to 3.0 equiv with respect to the compound of formula (2). Particularly, it is good to use the compound of formula (3) wherein R is saturated-$C_1$–$C_4$-alkyl. Among the alkyl-haloacetate, isopropyl-haloacetate is better than methyl- or ethyl-haloacetate, and t-butyl-haloacetate is better than isopropyl-haloacetate in terms of yield.

The zinc metal is preferably used in an amount of 1.0 to 3.0 equiv with respect to the compound of formula (2). The zinc metal is usually stirred with solvent under reflux at a temperature ranging from 20 to 120° C. It is preferable to use zinc dust or zinc powder.

As an organic acid or its derivative for activating the zinc metal, it is preferable to use $R^3CO_2H$, $R^3SO_3H$, $R^3CO_2TMS$, $R^3SO_3TMS$, or $(R^3SO_2)_2NH$ wherein $R^3$ represents hydrogen, saturated-$C_1$–$C_6$-alkyl, unsaturated-$C_2$–$C_6$-alkyl, saturated-$C_1$–$C_6$-alkyl substituted by halogen, unsaturated-$C_2$–$C_6$-alkyl substituted by halogen, $C_6$–$C_{12}$-aromatic or $C_6$–$C_{12}$-aromatic substituted by halogen in 0.001 to 0.1 equiv with respect to the compound of formula (2).

Aqueous hydrochloric acid or sulfuric acid may be used in the hydrolysis reaction step and hydrochloric acid is more suitable. It is preferable to adjust the pH of the reaction solution to 3 to 4 in the aspect of purity and yield. The aqueous acid solution is added dropwise at a temperature ranging from 0 to 5° C., and it is preferable to be stirred for hydrolysis at the same temperature.

The process according to the present invention provides advantages over the known precedents: 1) side products formation is minimized, 2) all the reactions are executed at around ambient temperature or above, 3) minimal use of reagents, α-haloacetate compound and zinc, is accomplished by employing the organic acid mediated activation.

All these improvements should lead to efficient execution of the process, and increased quality and yield of the product.

The present invention will be more specifically explained by the following example.

EXAMPLES

Example 1

Preparation of
(S)-6-chloro-5-hydroxy-3-oxo-hexanoic acid
t-butylester

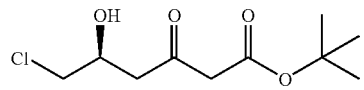

Zinc dust (690 mg), tetrahydrofuran (4.0 mL), and methanesulfonic acid (10 mg) were introduced into a reaction vessel and the mixture was stirred under reflux. To the mixture was added (S)-4-chloro-3-trimethylsilanyloxybutyronitrile (1.00 g) and subsequently t-butylbromoacetate (2.04 g) over 1 hour. The mixture was stirred under reflux for 30 minutes, and cooled to 0° C. Aqueous 3 N hydrochloric acid solution was added dropwise until the acidity of the reaction solution became pH 4, and the reaction solution was stirred for 3 hours. After the completion of reaction, tetrahydrofuran was distilled off under reduced pressure, and the residue was extracted with ethyl acetate and purified by silica gel column chromatography (eluent: ethyl acetate/n-hexane=⅓, v/v) to give the title compound in a yield of 87% (1.07 g).

$^1$H NMR (400 MHz, $CDCl_3$)δ

Enol form (7%): 12.40 (bs, 1H), 5.01 (s, 1H), 4.19 (m, 1H), 3.61 (m, 2H), 2.88 (m, 2H), 2.54 (m, 1H), 2.49 (bs, 1H), 2.47 (m, 1H), 1.49 (s, 9H).

Keto Form (93%): 4.32 (m, 1H), 3.62 (m, 2H), 3.42 (s, 2H), 3.00 (bd, 1H), 2.8 (m, 2H), 1.48 (s, 9H).

Mass (ESI, m/z): 497 (2M+Na+2), 495 (2M+Na), 261 (M+Na+2), 259 (M+Na).

The invention claimed is:

1. A process for preparing a compound of formula (1)

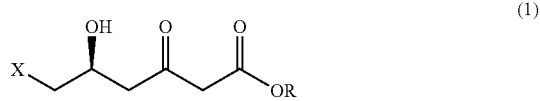

or its tautomer, in which

R represents hydrogen, saturated-$C_1$–$C_4$-alkyl, or unsaturated-$C_2$–$C_4$-alkyl, and X represents halogen, which comprises the following steps:

1) (S)-4-halo-3-hydroxybutyronitrile derivative of the following formula (2)

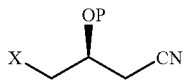 (2)

in which
X is as defined above, and
P represents hydrogen or a hydroxy-protecting group, is reacted with an α-haloacetate compound of the following formula (3)

 (3)

in which
R is as defined above, and
Y represents Br or I, in the presence of zinc metal activated by an organic acid or its derivative in an organic solvent and 2) the product of step 1) is hydrolyzed in the presence of aqueous acid solution.

2. The process of claim 1 wherein P of the (S)-4halo-3-hydroxybutyronitrile derivative of formula (2) represents hydrogen, or represents $SiRR^1R^2$ wherein R is as defined in claim 1, and $R^1$ and $R^2$ each represent hydrogen, saturated-$C_1$–$C_6$-alkyl, unsaturated-$C_2$–$C_6$-alkyl, or $C_6$–$C_{12}$-aromatic group, or represents ethoxyethyl or tetrahydropyranyl.

3. The process of claim 2 wherein P represents trimethylsilyl, triethylsilyl, t-butyldimethylsilyl, or t-butyldiphenylsilyl.

4. The process of claim 3 wherein P represents trimethylsilyl.

5. The process of claim 1 wherein the organic solvent is one or more selected from a group consisting of tetrahydrofuran, benzene, toluene, and ether.

6. The process of claim 5 wherein the organic solvent is tetrahydrofuran.

7. The process of claim 1 wherein R of the α-haloacetate compound of formula (3) represents saturated-$C_1$–$C_4$-alkyl.

8. The process of claim 7 wherein R represents t-butyl.

9. The process of claim 1 or 7 wherein the α-haloacetate compound of formula (3) is used in an amount of 1.0 to 3.0 equiv with respect to the compound of formula (2).

10. The process of claim 1 wherein the zinc metal is used in an amount of 1.0 to 3.0 equiv with respect to the compound of formula (2).

11. The process of claim 10 wherein the zinc metal is zinc dust or zinc powder.

12. The process of claim 1 wherein the organic acid or its derivative is selected from a group consisting of $R^3CO_2H$, $R^3SO_3H$, $R^3CO_2TMS$, $R^3SO_3TMS$, and $(R^3SO_2)_2NH$ wherein $R^3$ represents hydrogen, saturated-$C_1$–$C_6$-alkyl, unsaturated-$C_2$–$C_6$-alkyl, saturated-$C_1$–$C_6$-alkyl substituted by halogen, unsaturated-$C_2$–$C_6$-alkyl substituted by halogen, $C_6$–$C_{12}$-aromatic, or $C_6$–$C_{12}$-aromatic substituted by halogen.

13. The process of claim 12 wherein the organic acid or its derivative is used in an amount of 0.001 to 0.1 equiv with respect to the compound of formula (2).

14. The process of claim 1 wherein the aqueous acid solution is aqueous hydrochloric or sulfuric acid solution.

15. The process of claim 1 wherein the aqueous acid solution is added in an amount to adjust the pH to 3~4.

16. The process of claim 15 wherein the aqueous acid solution is added dropwise at a temperature ranging from 0 to 5° C.

* * * * *